(12) United States Patent
Davis (10) Patent No.: US 10,722,265 B1
(45) Date of Patent: Jul. 28, 2020

(54) EXPANDABLE AND COLLAPSIBLE BRAIN CANNULA

(71) Applicant: Rebound Therapeutics Corporation, Irvine, CA (US)

(72) Inventor: Peter G. Davis, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 17 days.

(21) Appl. No.: 15/701,278

(22) Filed: Sep. 11, 2017

Related U.S. Application Data (60) Provisional application No. 62/385,918, filed on Sep. 9, 2016.

(51) Int. Cl.
*A61B 1/32* (2006.01)
*A61B 17/34* (2006.01)

(52) U.S. Cl.
CPC ...... *A61B 17/3431* (2013.01); *A61B 17/3423* (2013.01); *A61B 17/3439* (2013.01); *A61B 2017/3425* (2013.01)

(58) Field of Classification Search
CPC ............ A61B 17/3431; A61B 17/3423; A61B 17/3439; A61B 17/3425; A61B 17/3427; A61B 17/3429
USPC ......... 600/201–249, 114, 121; 606/190–191, 606/198
See application file for complete search history.

(56) References Cited

U.S. PATENT DOCUMENTS

| | | | | |
|---|---|---|---|---|
| 5,527,264 A | * | 6/1996 | Moll | A61B 17/0218 600/204 |
| 5,865,728 A | * | 2/1999 | Moll | A61B 17/0218 600/204 |
| 9,216,015 B2 | * | 12/2015 | Wilson | A61B 17/3431 606/190 |
| 2009/0048622 A1 | * | 2/2009 | Wilson | A61B 17/3431 606/190 |
| 2011/0021879 A1 | * | 1/2011 | Hart | A61B 17/0293 600/207 |
| 2011/0021881 A1 | * | 1/2011 | Wenchell | A61B 17/34 600/227 |
| 2011/0144442 A1 | * | 6/2011 | Farrell | A61B 1/32 600/206 |
| 2011/0144448 A1 | * | 6/2011 | Shelton, IV | A61B 17/3423 600/216 |
| 2013/0178709 A1 | * | 7/2013 | Suh | A61B 17/0293 600/205 |
| 2017/0347865 A1 | * | 12/2017 | Chen | A61B 17/00234 606/192 |

* cited by examiner

*Primary Examiner* — Jessica Weiss
(74) *Attorney, Agent, or Firm* — Crockett & Crockett, PC; K. David Crockett, Esq.

(57) ABSTRACT

A method of accessing a target site within the brain of a patient, through the skull of the patient, with an expandable cannula.

6 Claims, 9 Drawing Sheets

EXPANDABLE AND COLLAPSIBLE BRAIN CANNULA

The application claims priority to U.S. Provisional Application 62/385,918, filed Sep. 9, 2016.

FIELD OF THE INVENTIONS

The inventions described below relate to the field of minimally invasive brain surgery.

BACKGROUND OF THE INVENTIONS

Stroke is a common cause of death and disabling neurologic disorder. Approximately 700,000 patients suffer from stroke in the United States every year. Hemorrhagic stroke accounts for 20% of the annual stroke population. Hemorrhagic stroke is due to a rupture of a blood vessel in the brain, causing bleeding into the brain tissue and resulting in a hematoma (a blood mass) in the brain. Prompt removal of the blood mass is necessary to limit or prevent long-term brain injury. Removal of the blood mass requires access through the skull and brain tissue, and this is usually accomplished by inserting a cannula through a small burr hole in the skull (created by a drill), or a larger hole created with a saw (a craniotomy or craniotomy hole), and forcing the cannula through the brain. To minimize trauma to the brain, this is currently accomplished with a cannula and obturator assembly, in a method that entails pushing a fairly large cannula, with an obturator disposed in the lumen of the cannula and protruding distally from the cannula, into the brain, using the tip of the obturator to push aside brain tissue to minimize trauma.

Wilson, Apparatus and Methods for Performing Brain Surgery, WO2006/050047 (Nov. 5, 2006) proposed inserting a small diameter expandable sleeve over a stylet, followed by forcing a larger diameter cannula down into the sleeve. Translation of the rigid cannula down into the sleeve serves to gradually expand the sleeve, from the proximal end (nearest the entry point) to the distal end (nearest the target site) and gently retract the brain. Also, Wilson discloses inserting a tube comprising expandable braid covered in an expandable sleeve, in a small diameter configuration, and pushing on both the proximal and distal ends of the braid to force it expand and foreshorten, to create a large lumen tube in the brain.

SUMMARY

The devices and methods described below provide for easier access to surgical sites in the brain. The device comprises an expandable and collapsible brain cannula which can be inserted into the brain in a small diameter configuration compacted within a constraining tube, inserted to a desired depth near a target site such as a blood mass, and released from the tube to allow it to expand to a large diameter configuration and thereby provide a cannula large enough to permit passage of the distal end of tools such as aspirators, macerators, ablation devices, stimulation electrodes, drug delivery devices or drains and the like through the cannula and into the surgical site. The cannula comprises a tube, braid or coil of resilient material, which is flexible enough to be compacted into a small diameter configuration to fit into an insertion tube, and resilient enough to expand within the brain, gently expanding against surrounding brain tissue, to a large diameter configuration upon release from the insertion tube. The device may be made of pseudoelastic nitinol, shape memory nitinol, stainless steel, spring steel, and resilient polymers (including biodegradable polymers), etc. The tube may be covered with an elastic sheath, to prevent intrusion of brain tissue into any gaps between filaments of a braid, turns of a coil, or gaps in a laser cut tube. In use, the cannula is compressed into a small diameter tube, and pushed through brain tissue (preferably through the sulcus between folds or gyrus of the brain), and the small diameter tube is withdrawn over the cannula to allow the cannula to expand. To remove the cannula, a small diameter tube may be gradually slipped over the cannula, as the cannula is held steady to avoid sliding against brain tissue, until the entire cannula is compressed within the tube, whereupon the tube and compacted cannula are removed from the brain.

DETAILED DESCRIPTION OF THE INVENTIONS

Figure 1:
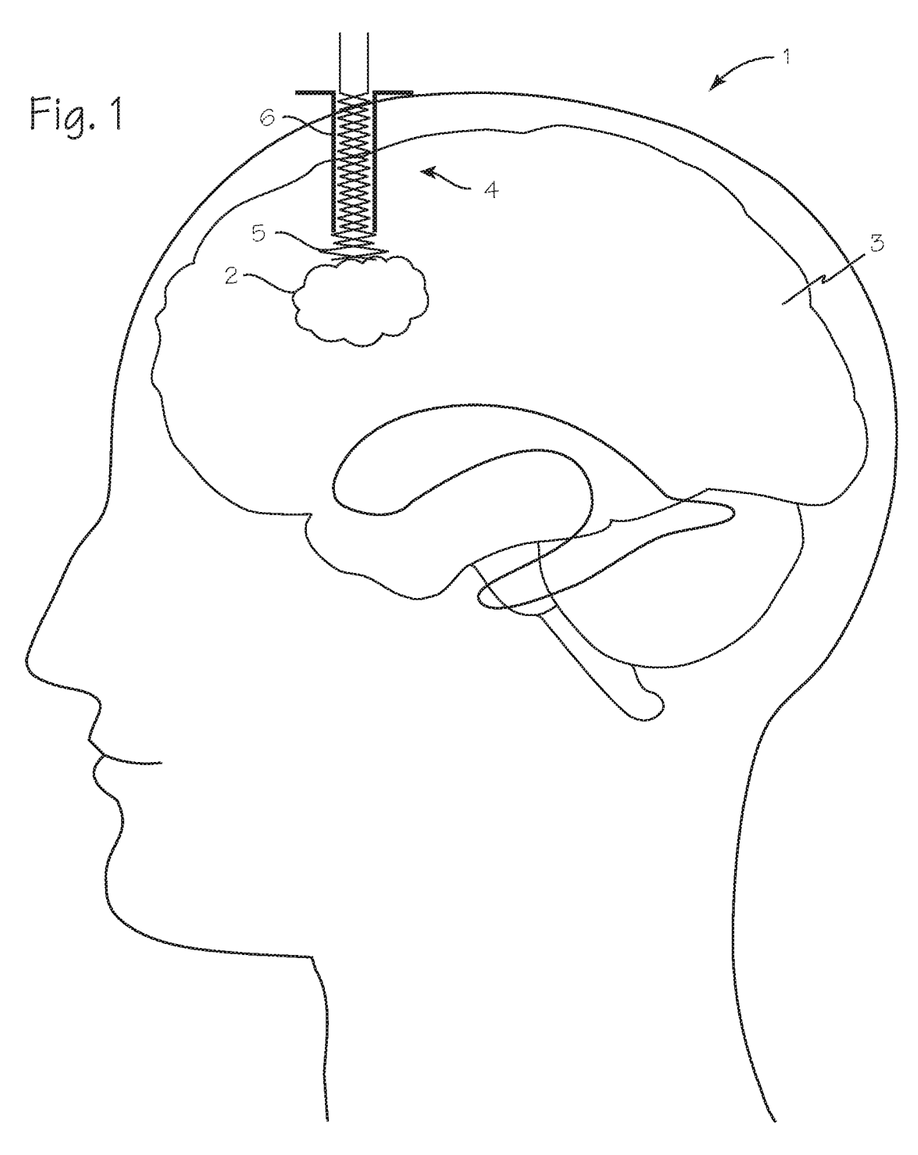
FIG. 1 illustrates a patient with an intracerebral hematoma, and an expandable cannula in place to provide access to the hematoma.

FIG. 1 illustrates a patient 1 with a blood mass 2 in the brain 3 that necessitates surgical intervention. An expandable cannula system 4 has been inserted into the brain, with the distal end of the cannula proximate the blood mass. The cannula system includes an expandable cannula 5 surrounded by an insertion tube 6, which, as described below, functions to constrain the cannula in a small diameter configuration. As depicted in FIG. 1, the cannula is in its small diameter configuration, and constrained by the insertion tube.

Figure 2:
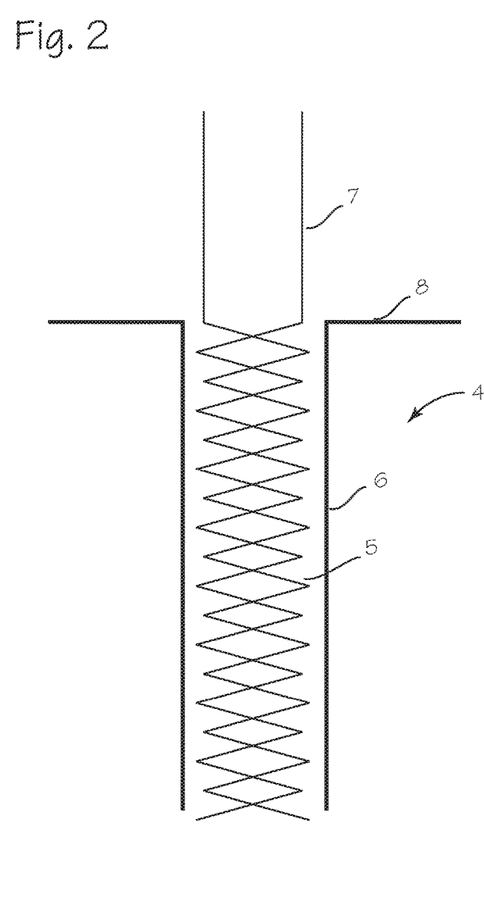
FIG. 2 illustrates a cannula system, with a cannula which is expandable and compressible, to expand from a small diameter configuration to a large diameter configuration, and also compress from a large diameter configuration to a small diameter configuration.

FIG. 2 illustrates a cannula system, with the cannula 5 which is expandable and compressible, to expand from a small diameter configuration to a large diameter configuration, and also compress from a large diameter configuration to a small diameter configuration. The cannula 5 comprises a resiliently expandable tube, which may be a solid-walled tube, a tube with numerous apertures in its wall, a braided tube, a coil of resilient material, or a series of spring loaded inter-digitated sectioning pieces which is flexible enough to be compacted into a small diameter configuration to fit into an insertion tube, and resilient enough to expand within the brain, gently expanding against surrounding brain tissue, to a large diameter configuration upon release from the insertion tube. As depicted in FIG. 2, the cannula is in its small diameter configuration, and constrained by the insertion tube. The unconstrained, large diameter configuration may be uniform throughout the length of the cannula. The device may be made of pseudoelastic nitinol (pseudoelastic at body temperature), shape memory nitinol, stainless steel, spring steel, resilient polymers (including biodegradable polymers), etc. Preferably, the tube comprises a pseudoelastic nitinol tube, laser-cut to remove much of the wall material. The tube may be covered with an elastic or hydrogel sheath, to prevent intrusion of brain tissue into any gaps between filaments of a braid, turns of a coil, or gaps in a laser cut tube.

The cannula is compressed within the insertion tube 6, which has a small inner diameter to allow for easy insertion into the brain. The cannula may include one or more posts or pushwires 7, disposed at the proximal end of the cannula and extending proximally from the cannula, for use in holding the cannula steady while the insertion tube is withdrawn proximally to allow the cannula to expand. The posts may be permanently fixed to the cannula, and may comprise a continuation of a braid of the cannula, or they may be releasably attachable to the cannula. Preferably, the length of the insertion tube is shorter than the length of the posts, so that the tube may be slipped over the posts, and the posts may be grasped by the surgeon to hold the cannula in place, preventing unwanted inward or outward motion of the cannula, while the surgeon is pulling the insertion tube outwardly to release the cannula, or pushing the insertion tube inwardly to recapture the cannula. The length of the posts needs to be sufficient to extend from the proximal end of the insertion tube or extraction tube when a proximal portion of the cannula is disposed within the distal end of the insertion tube or extraction tube. A flange (or one or more tabs) 8 is disposed on the insertion tube proximal end, for use in pulling the insertion tube proximally to uncover the cannula. The insertion tube may be scored along its length, so that upon withdrawal it may be torn open, so that the post(s) 7 may be shorter than the insertion cannula.

For access to a typical hematoma in the brain, the cannula may be 2 to 20 cm long, with an unrestrained diameter of about 6 to 60 mm, a wall-thickness of about 0.1 to 1 mm, depending on the material chosen. Preferably, the cannula is fabricated to provide a hoop strength of about 3.5N when unconstrained, or total outward force of about 2 to 5N (0.4 to 1 lb.) and more preferably about 3 to 4 N, or an average outward force of about 5 N/mm2, or 725 psi). The insertion tube is preferably about 1 to 3 mm in outer diameter, and 1.5 to 2.5 mm in inner diameter, and the cannula is compressible to a small diameter configuration which fits into the insertion cannula.

Figure 3:
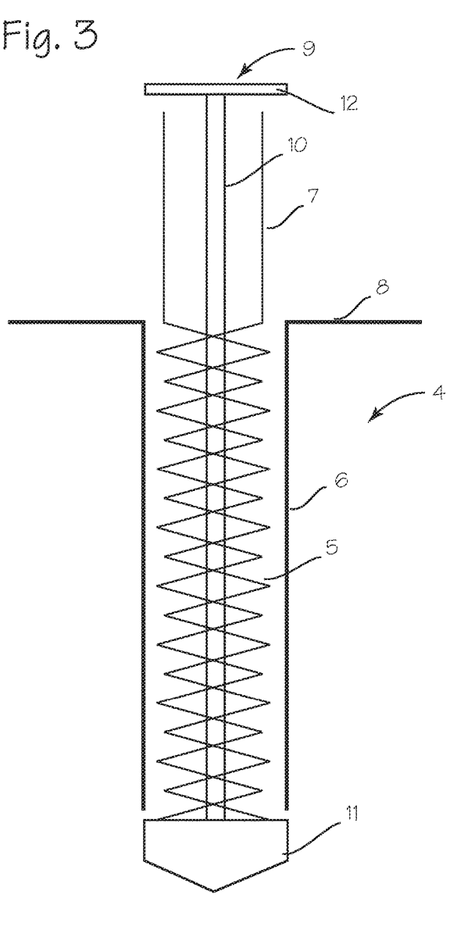
FIG. 3 illustrated the cannula system of FIG. 2, modified with the addition of an obturator.

FIG. 3 illustrated the cannula system of FIG. 2, modified with the addition of an obturator. The system of FIG. 3 includes all the components of the system of FIG. 2, and also includes an obturator 9. The obturator comprises a rod segment 10 with a small diameter that fits within the cannula in its compressed, small diameter configuration, and a large diameter conical tip 11. The tip has a proximally facing shoulder, which abuts the distal end of the cannula when the cannula is in its compressed, small diameter configuration within the insertion tube. The proximally facing shoulder has an outer diameter slightly larger (perhaps as large as the outer diameter of the insertion tube) than the inner diameter of the cannula in its compressed configuration, so that the cannula cannot translate distally (deeper into the brain) relative to obturator while in its compression configuration. The obturator may have a small flange 12 or other structure at its proximal end to serve as a handle, and to serve as a mount for sensors operable for registration with a neuro-navigation system.

In use, the cannula is compressed into a small diameter insertion tube, and pushed through brain tissue (preferably between gyrus of the brain, avoiding puncturing gray matter to the extent possible), and the small diameter tube is withdrawn over the cannula to allow the cannula to expand. To remove the cannula, the small diameter tube may be gradually advanced over the cannula, as the cannula is held steady to avoid sliding against brain tissue, until the entire cannula compressed with the tube, whereupon the tube and compacted cannula are removed from the brain.

The procedure is illustrated in FIGS. 4 through 10.

Figure 4:
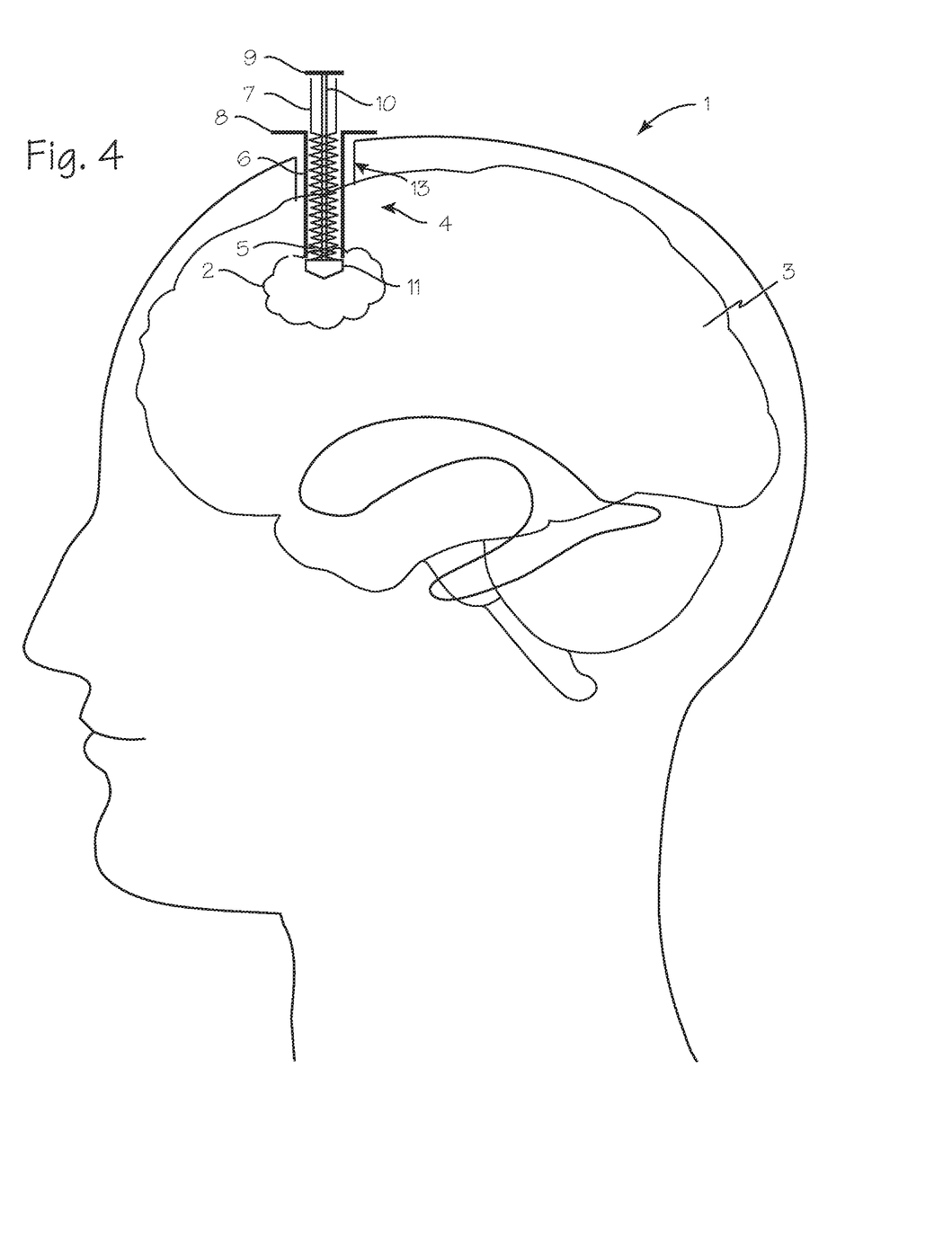
FIG. 4 illustrates initial placement of the cannula system.

FIG. 4 illustrates initial placement of the cannula system. As shown in FIG. 4, a surgeon has inserted the assembled cannula system, through a burr hole 13, into the brain, so that the distal end of the assembled cannula assembly is near a target site within the brain (the hematoma).

Figure 5:
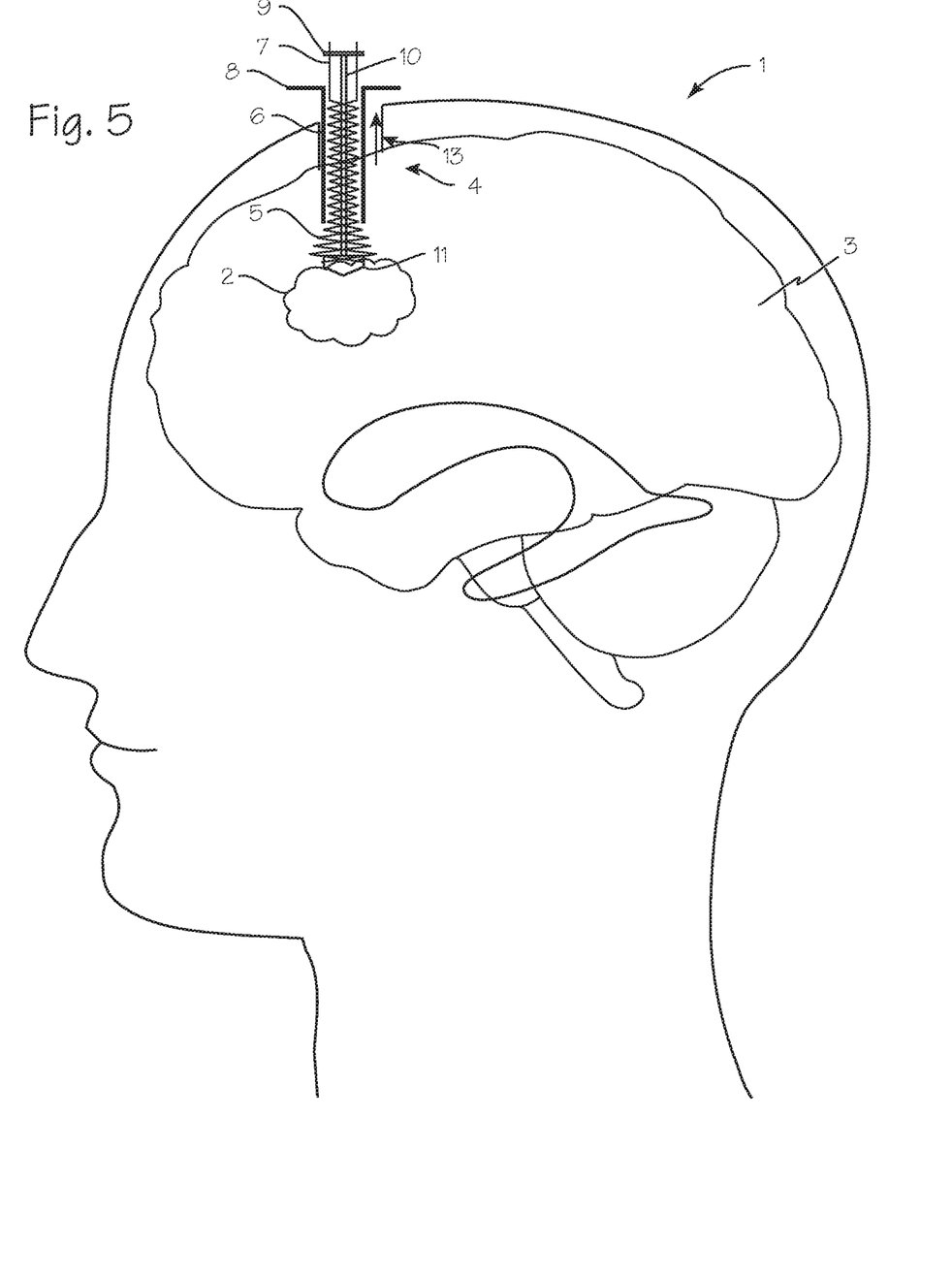
FIG. 5 illustrates pull-back of the delivery tube of the cannula system to release the expandable cannula.

FIG. 5 illustrates the initial pull-back of the insertion tube of the cannula system to release the expandable cannula. As shown in FIG. 5, the surgeon has pulled the insertion tube proximally, while holding the cannula steady to avoid distal or proximal translation of the cannula (that is, movement along the longitudinal axis of the cannula) that might result in sliding the cannula over or through brain tissue. The surgeon may hold the cannula in place by grasping the post(s) 7. While holding the cannula steady, the surgeon pulls the insertion tube proximally, by pulling on the tab(s) 8. As the insertion tube moves proximally, the cannula is gradually released from its constraint, and expands gradually, from the distal end to the proximal end. If an obturator is used, as the cannula expands, the inner diameter of the cannula will grow to exceed the diameter of the obturator. The obturator can pulled proximally, so that the proximal face abuts a portion of the cannula still constrained by the insertion tube. Alternatively, the surgeon may hold the obturator and cannula, at their proximal ends, so as to fix the obturator longitudinally relative to the cannula.

Figure 6:
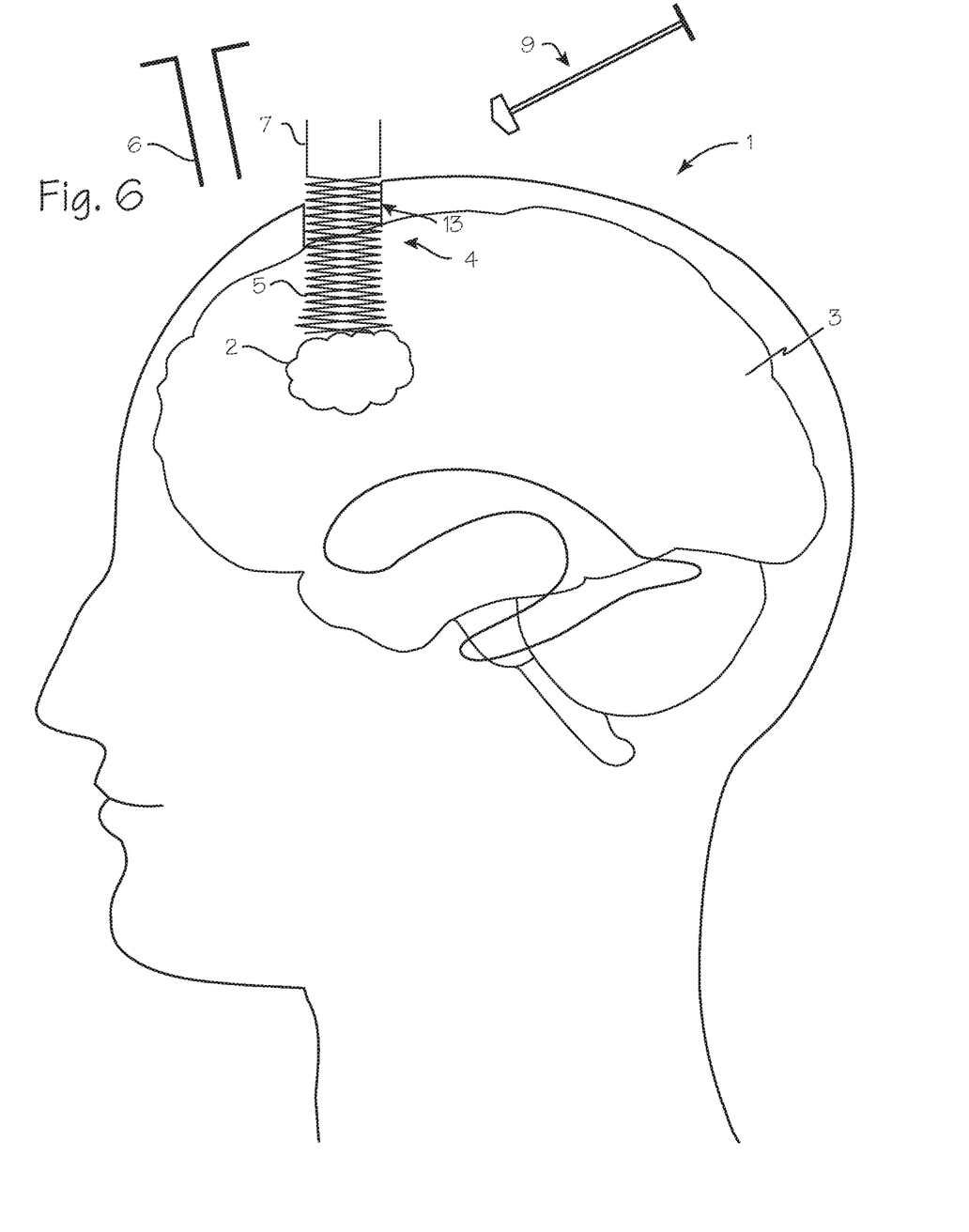
FIG. 6 illustrates removal of an obturator, after expansion of the cannula.

FIG. 6 illustrates removal of an obturator, after expansion of the cannula. In FIG. 6, the insertion tube has been completely removed and the obturator has been removed from the lumen of the cannula. The cannula is unconstrained by the insertion tube, and has expanded toward its unconstrained large diameter configuration. Expansion of the cannula may be limited by the surrounding brain tissue, or the bone surrounding the burr hole.

Figure 7:
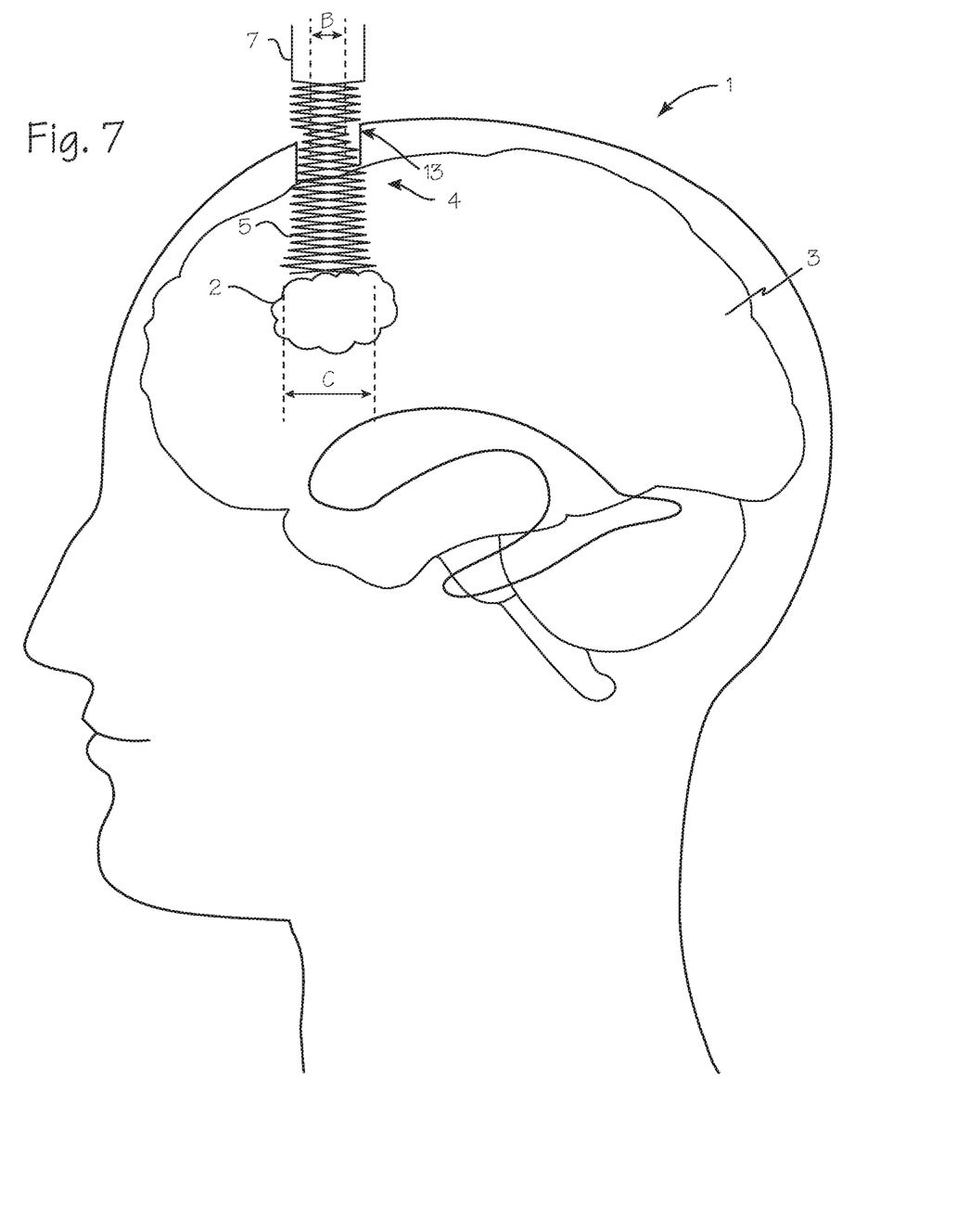
FIG. 7 illustrates a configuration of the cannula, after removal of the sheath.

FIG. 7 illustrates a configuration of the cannula, after removal of the sheath. In this illustration, a small bore burr hole has been created in the skull of the patent, and the expandable cannula has been inserted and the insertion tube removed to allow the cannula to expand. The unconstrained diameter of the cannula in this illustration is larger than the diameter B of the burr hole created by the surgeon, so that, upon expansion within the brain, the cannula expands toward its unconstrained diameter, to achieve a large diameter configuration which is larger diameter C than the burr hole, except where constrained by the skull surrounding the burr hole.

Figure 8:
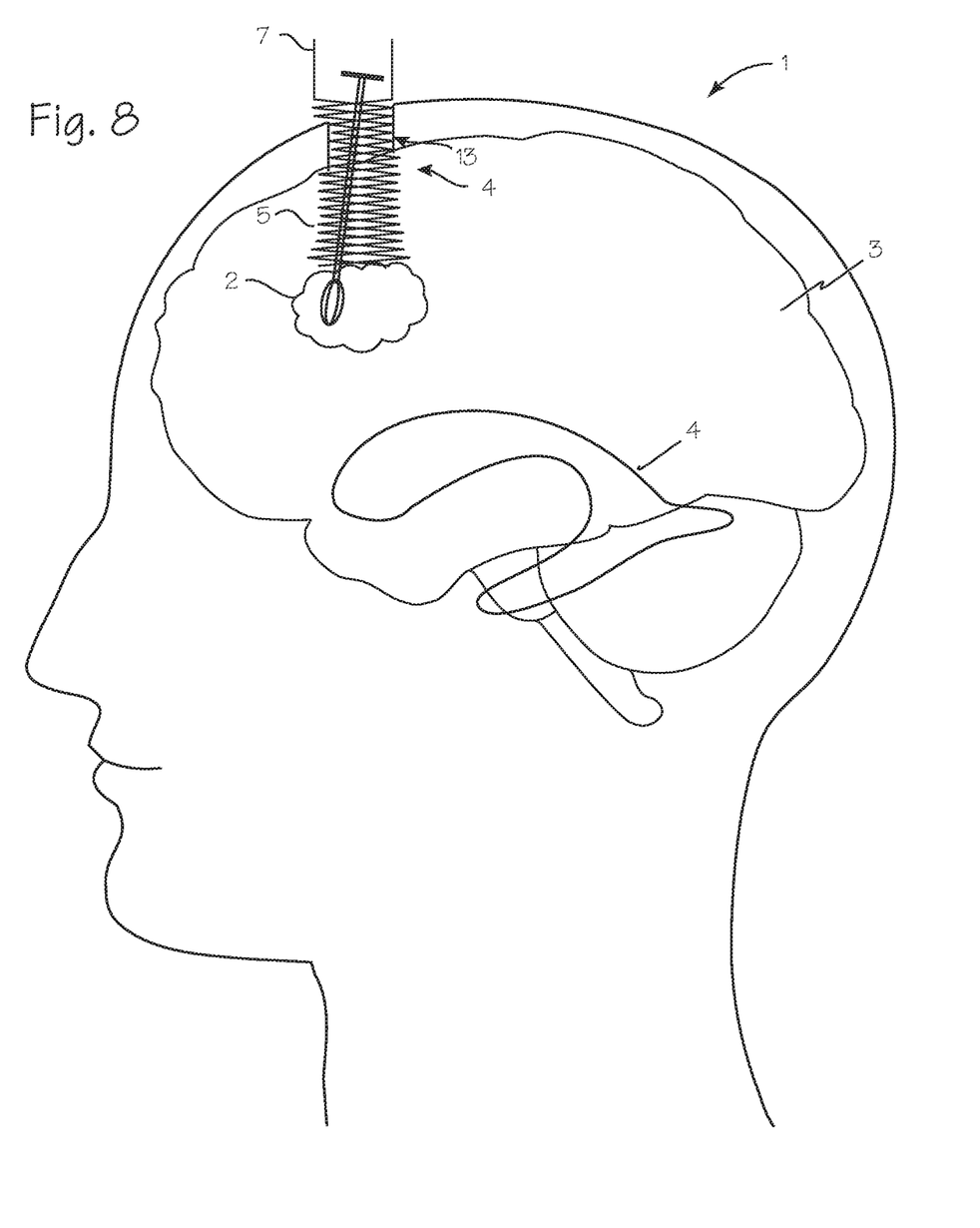
FIG. 8 illustrates the use of a surgical tool through the expanded cannula.

FIG. 8 illustrates the use of a surgical tool through the expanded cannula. With the cannula in a large diameter configuration, the surgeon may insert the distal end of any suitable surgical device through the cannula and into the target site, such as the hematoma.

Figure 9:
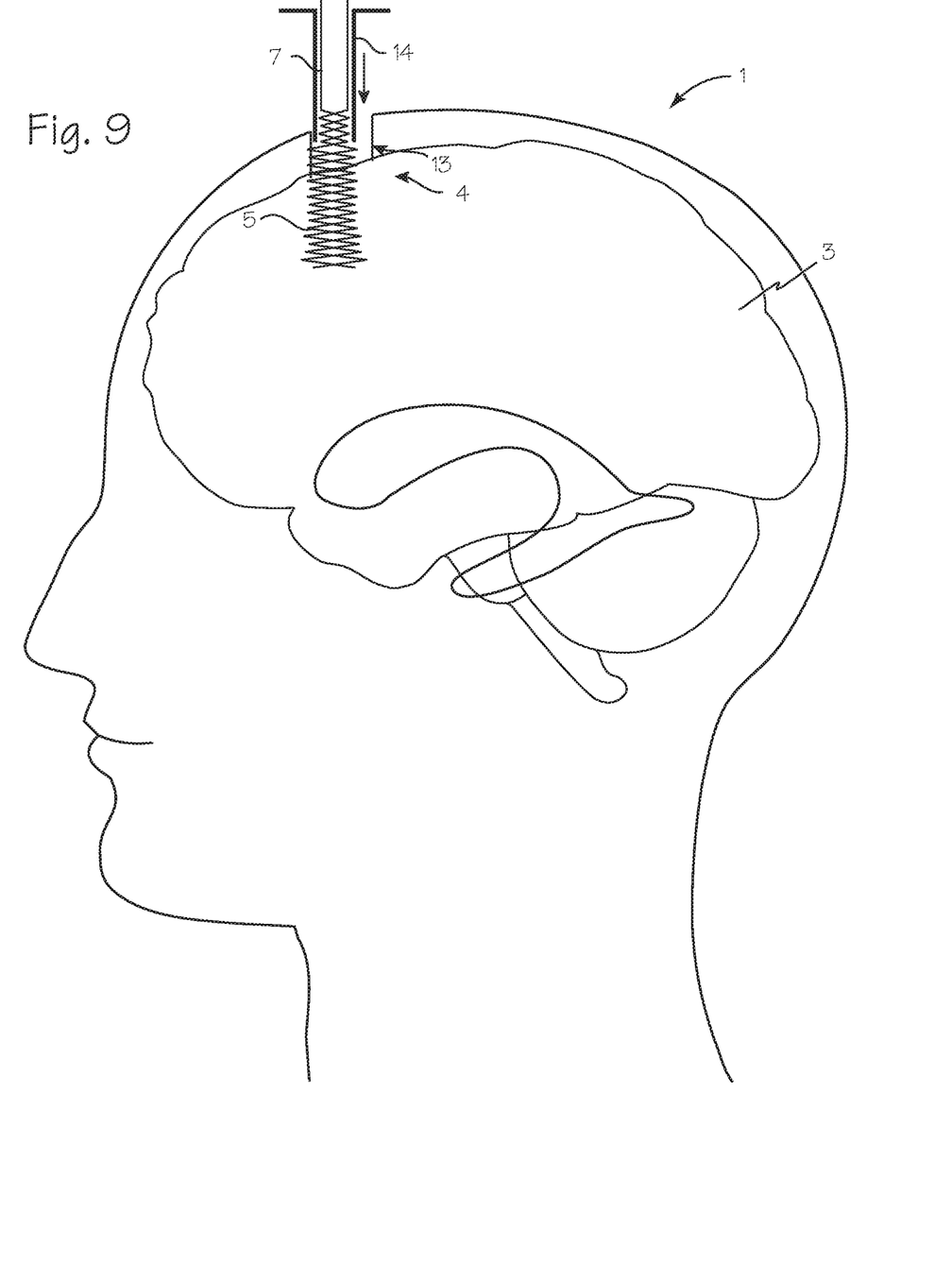
FIG. 9 illustrates an initial step in the recapture of the cannula and its compression into the delivery tube.

FIG. 9 illustrates an initial step in the recapture of the cannula and its compression into the delivery tube, to be performed after the blood mass has been removed (or other intracranial procedure has been completed). As shown in FIG. 9, the surgeon slips an extraction tube 14 over the post(s) 7 and the proximal end of the cannula, and gradually forces the extraction tube distally over the cannula. The surgeon holds the posts, to prevent the cannula from translating distally (further into the brain) due to the force applied by the extraction tube. Preferably, the surgeon also prevents the cannula from moving proximally, to avoid sliding the cannula outer wall over brain tissue. The extraction tube may be the very tube used as the insertion tube, or a new tube. If a new tube is used, it may have a larger diameter than the insertion tube, since it may not be necessary to compact the cannula to the same small diameter that facilitates insertion.

Figure 10:
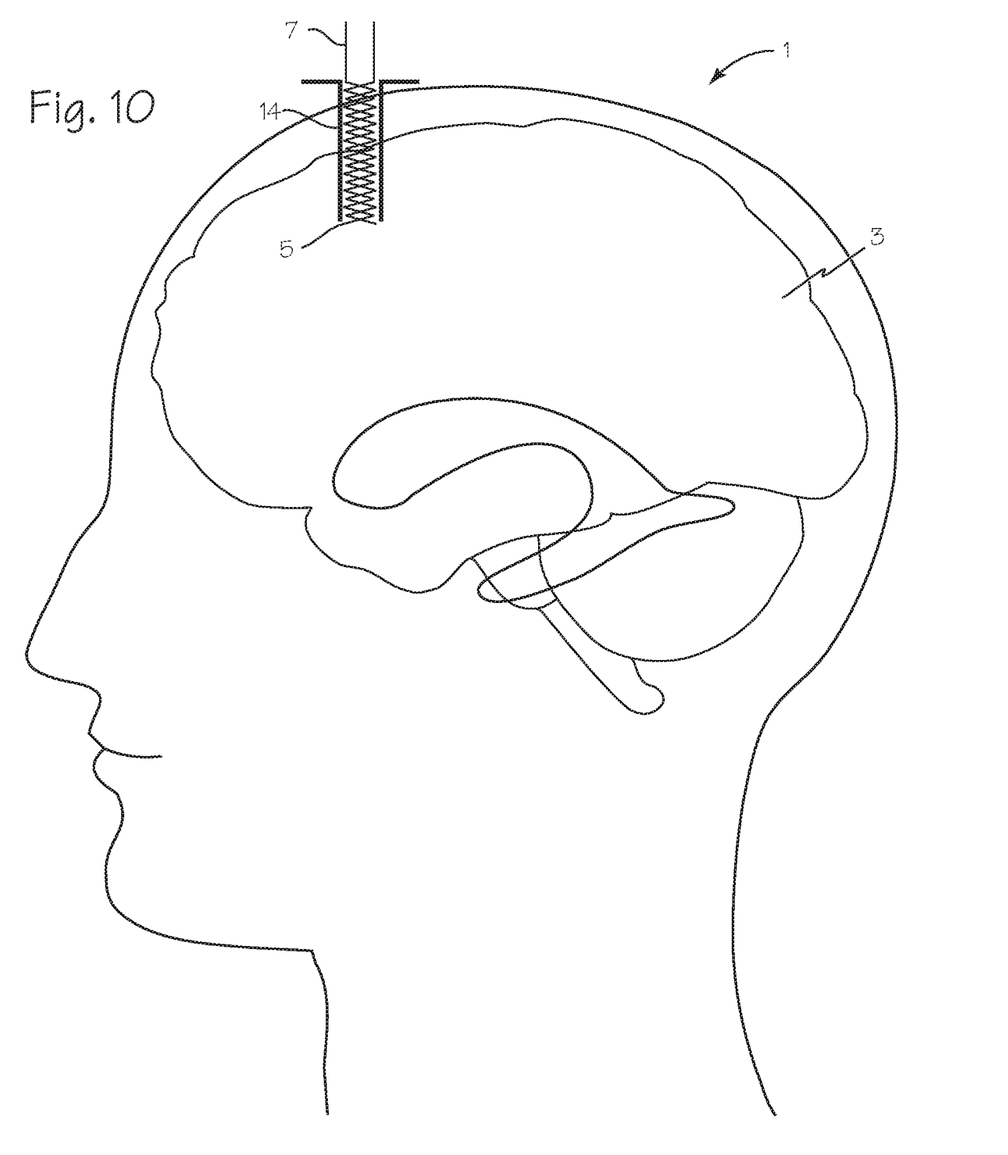
FIG. 10 illustrates the configuration of the cannula system after the delivery tube has been slipped over the entirety of the cannula and compressed the cannula into its small diameter configuration.

FIG. 10 illustrates the configuration of the cannula system after the delivery tube has been slipped over the entirety of the cannula and compressed the cannula into its small diameter configuration. At the end of this step, the cannula has been compressed along its entire length to a small diameter configuration and cannula system, including the cannula and the tube, may be removed from the brain.

As depicted in the figures, the device facilitates a method of accessing a target site within the brain of a patient, through the skull of the patient. The method, performed by a surgeon, entails providing the expandable and collapsible cannula, characterized by a small diameter configuration and an unconstrained large diameter configuration, with the cannula disposed in the small diameter insertion tube in its small diameter configuration, and inserting the cannula, while disposed in the insertion tube, through an opening in the skull of the patient, and pushing the cannula distally through brain tissue until a distal end of the cannula is proximate the target site. To expand the cannula, the surgeon pulls the insertion tube proximally while preventing the cannula from moving distally, to allow the cannula to resiliently expand toward its large diameter configuration, to the extent permitted by surrounding brain tissue. With the cannula in place and opened to a large diameter configuration, the surgeon will insert the distal end of a surgical instrument through the cannula and into the target site. After performing a surgical procedure, such as aspiration of a blood mass, the surgeon can remove the cannula by compressing the proximal end of the cannula and advancing a tube having a diameter smaller than the cannula in its expanded configuration over the cannula, to compress the cannula toward its small diameter configuration, and then pulling the cannula proximally to withdraw the cannula from the brain.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method of accessing a target site within a brain of a patient, through a skull of the patient, said method comprising:
   providing an expandable and collapsible cannula, said cannula comprising a resiliently expandable tube, said cannula having a small diameter configuration and an unconstrained large diameter configuration, said cannula disposed in an insertion tube in said small diameter configuration;
   inserting the cannula, while disposed in the insertion tube, through an opening in the skull of the patient, and pushing the cannula distally through brain tissue until a distal end of the cannula is proximate the target site; and
   pulling the insertion tube proximally while preventing the cannula from moving distally, to allow the cannula to expand toward its large diameter configuration.

2. The method of claim 1 further comprising the steps of:
   inserting a distal end of a surgical instrument through the cannula and into the target site.

3. The method of claim 1 further comprising the steps of:
   compressing a proximal end of the cannula and advancing an extraction tube having a diameter smaller than the cannula in its large diameter configuration over the cannula, to compress the cannula toward its small diameter configuration; and
   withdrawing the cannula from the brain.

4. The method of claim 3 further comprising the steps of:
   providing the proximal end of the cannula with a post extending proximally from the cannula;
   and accomplishing the step of compressing the proximal end of the cannula and advancing the extraction tube over the cannula by advancing the extraction tube over the post, grasping the post to limit distal movement of the cannula, and thereafter advancing the extraction tube over the cannula.

5. The method of claim 1 further comprising the steps of:
   compressing a proximal end of the cannula and advancing the insertion tube over the cannula in its large diameter configuration, to compress the cannula toward its small diameter configuration; and
   withdrawing the cannula from the brain.

6. The method of claim 5 further comprising the steps of:
   providing the proximal end of the cannula with a post extending proximally from the cannula;
   and accomplishing the step of compressing the proximal end of the cannula and advancing the insertion tube over the cannula by advancing the insertion tube over the post, grasping the post to limit distal movement of the cannula, and thereafter advancing the insertion tube over the cannula.

* * * * *